United States Patent
Nakao et al.

(10) Patent No.: US 8,303,612 B2
(45) Date of Patent: Nov. 6, 2012

(54) INTRAVASCULAR FOREIGN MATTER REMOVING WIRE AND MEDICAL IMPLEMENT

(75) Inventors: Koji Nakao, Tokyo (JP); Hideshi Obitsu, Kanagawa (JP); Takeshi Kanamaru, Kanagawa (JP)

(73) Assignee: Terumo Kabushiki Kaisha, Shibuya-Ky, Tokyo (JP)

( * ) Notice: Subject to any disclaimer, the term of this patent is extended or adjusted under 35 U.S.C. 154(b) by 610 days.

(21) Appl. No.: 11/921,935

(22) PCT Filed: Jun. 7, 2006

(86) PCT No.: PCT/JP2006/311407
§ 371 (c)(1),
(2), (4) Date: Jul. 29, 2009

(87) PCT Pub. No.: WO2006/137267
PCT Pub. Date: Dec. 28, 2006

(65) Prior Publication Data
US 2010/0016875 A1    Jan. 21, 2010

(30) Foreign Application Priority Data

Jun. 20, 2005  (JP) ................................. 2005-179869

(51) Int. Cl.
*A61B 17/22* (2006.01)
(52) U.S. Cl. ......................... 606/159; 606/113; 606/127
(58) Field of Classification Search .................. 606/110, 606/113, 114, 127, 128, 159, 200
See application file for complete search history.

(56) References Cited

U.S. PATENT DOCUMENTS

| | | | |
|---|---|---|---|
| 3,108,593 A | 10/1963 | Glassman | |
| 3,108,594 A | 10/1963 | Glassman | |
| 5,100,423 A | 3/1992 | Fearnot | |
| 5,902,263 A * | 5/1999 | Patterson et al. | 604/22 |
| 6,245,087 B1 * | 6/2001 | Addis | 606/200 |
| 6,458,139 B1 | 10/2002 | Palmer et al. | |
| 6,872,211 B2 * | 3/2005 | White et al. | 606/114 |
| 2002/0002383 A1 | 1/2002 | Sepetka et al. | |
| 2003/0018355 A1 | 1/2003 | Goto et al. | |
| 2003/0191492 A1 | 10/2003 | Gellman et al. | |
| 2004/0133231 A1 * | 7/2004 | Maitland et al. | 606/200 |

FOREIGN PATENT DOCUMENTS

| | | |
|---|---|---|
| JP | 5-137729 | 6/1993 |
| JP | 9-313499 A | 12/1997 |
| JP | 2002-516139 A | 6/2002 |
| JP | 2002-282271 A | 10/2002 |
| JP | 2004-16668 A | 1/2004 |
| WO | WO 99/60933 A1 | 12/1999 |

OTHER PUBLICATIONS

International Search Report.

* cited by examiner

*Primary Examiner* — Ryan Severson
*Assistant Examiner* — Rachel S Papeika
(74) *Attorney, Agent, or Firm* — Buchanan Ingersoll & Rooney PC

(57) ABSTRACT

An intravascular foreign matter removing wire has a flexible long wire body, a first catching section located on the tip side of the wire body and operative to catch a foreign matter present inside a blood vessel, and a second catching section located in the vicinity of and on the base end side of the first catching section and operative to catch a foreign matter present inside a blood vessel.

17 Claims, 15 Drawing Sheets

INTRAVASCULAR FOREIGN MATTER REMOVING WIRE AND MEDICAL IMPLEMENT

TECHNICAL FIELD

The present invention relates to an intravascular foreign matter removing wire for removing foreign matter present inside a blood vessel and to a medical implement.

BACKGROUND ART

According to the vital statistics made by the Japanese Ministry of Health, Labor and Welfare, the first-ranked of the causes of death of Japanese is cancer, the second-ranked is cardiopathy, and the third-ranked is cerebral apoplexy. Particularly, the number of people dying from cerebral apoplexy and the number of people suffering from sequelae of cerebral apoplexy have been increasing, and there is a pressing need to establish a cure for cerebral apoplexy.

In recent years, in the cure of cerebral apoplexy, a thrombolytic cure based on the use of thrombolytics for curing cerebral infarct in acute phase has been developed and producing therapeutic effects, but a limitation of this cure is being pointed out. Specifically, it has been recognized from doctors' experiences that a long time may be taken for thrombolysis by a thrombolytic, a thrombus reduced in size may fly further to form a new thrombosis site, or there may be thrombi which cannot be dissolved by thrombolytics.

In the case of cerebral infarct, it has been verified in USA and Europe that not only the probability of survival is increased but also the probability of sequelae is reduced if the bloodstream can be recovered in three hours after the sideration of infarct. Therefore, there is a keen demand for the development of a medical implement which can be inserted into a cerebral blood vessel and by which a thrombus in the cerebral blood vessel can be directly removed.

As one of such medical implements, there has been proposed a medical recovering basket having a basket (foreign matter catching section) which is movable from a retracted position to an expanded position in relation to a sheath (catheter) (refer to, for example, JP-A-2002-516139).

This medical implement, however, has the problem that in the case where the foreign matter (thrombus) is comparatively soft, for example, the foreign matter (thrombus) would leak out through gaps present in a spiral leg constituting the basket, making it difficult to satisfactorily catch the foreign matter (thrombus).

DISCLOSURE OF INVENTION

It is an object of the present invention to provide an intravascular foreign matter removing wire, and a medical implement, with which it is possible to securely catch and remove a foreign matter present inside a blood vessel.

In order to attain the above object, according to the present invention, there is provided an intravascular foreign matter removing wire including:

a flexible long wire body;

a first catching section located on the tip side of the wire body and operative to catch a foreign matter present inside a blood vessel; and a second catching section located in the vicinity of and on the base end side of the first catching section and operative to catch a foreign matter inside a blood vessel.

This makes it possible to securely catch and remove a foreign matter present inside a blood vessel.

In addition, in the intravascular foreign matter removing wire according to the present invention, preferably, the first catching section is composed of at least two branch wire parts branched from the tip side of the second catching section, and a plurality of filament parts bridgingly disposed between two of the branch wire parts.

This configuration ensures that in the case where the foreign matter is composed of a central (core-forming) comparatively hard core part and a comparatively soft adherent part adhering to the outside surface of the core part, the core part can be easily stored into the first catching section, so that the core part can be caught assuredly.

Besides, in the intravascular foreign matter removing wire according to the present invention, preferably, the second catching section is coil-like in shape.

This configuration ensures that in the case where the foreign matter is composed of a central (core-forming) comparatively hard core part and a comparatively soft adherent part adhering to the outside surface of the core part, the adherent part comes into the gap between portions of the coil when the foreign matter is caught, so that the adherent part can be arrested (caught) assuredly.

In addition, in the intravascular foreign matter removing wire according to the present invention, preferably, the second catching section is composed of a plurality of loop-formed loop wires arrayed along the longitudinal direction of the wire body.

This configuration ensures that in the case where the foreign matter is composed of a central (core-forming) comparatively hard core part and a comparatively soft adherent part adhering to the outside surface of the core part, the core part is caught by the first catching section. In addition, the adherent part comes into the loop wires, so that the adherent part can be arrested assuredly.

Besides, in the intravascular foreign matter removing wire according to the present invention, preferably, the plurality of loop wires are so formed that their respective formation directions are substantially the same, when the second catching section is viewed from the tip side in the longitudinal direction of the wire body.

This configuration ensures that in the case where the foreign matter is composed of a central (core-forming) comparatively hard core part and a comparatively soft adherent part adhering to the outside surface of the core part, the core part is caught by the first catching section. Besides, the adherent part comes into the loop wires, so that the adherent part can be arrested assuredly.

In addition, in the intravascular foreign matter removing wire according to the present invention, preferably, at least adjacent ones of the loop wires are so formed that their respective formation directions are different, when the second catching section is viewed from the tip side in the longitudinal direction of the wire body.

This configuration ensures that in the case where the foreign matter is composed of a central (core-forming) comparatively hard core part and a comparatively soft adherent part adhering to the outside surface of the core part, the core part is caught by the first catching section. In addition, the adherent part comes into the loop wires, so that the adherent part can be arrested assuredly.

In addition, in the intravascular foreign matter removing wire according to the present invention, preferably, the second catching section is deformable, and the intravascular foreign matter removing wire further composes an operating wire for operating the second catching wire so as to deform the second catching section.

This configuration makes it possible to securely operate the second catching section so as to deform the second catching section.

Besides, in the intravascular foreign matter removing wire according to the present invention, preferably, the operating wire has its tip part joined to a tip part of the second catching wire, and the tip part of the second catching section is drawn and deformed toward a base end part of the second catching section by pulling the operating wire in the base end direction.

This configuration ensures that in the case where the foreign matter is composed of a central (core-forming) comparatively hard core part and a comparatively soft adherent part adhering to the outside surface of the core part and where the adherent part is present in the vicinity of the inside wall of a blood vessel, the adherent part is assuredly caught by the second catching section.

In addition, in the intravascular foreign matter removing wire according to the present invention, preferably, the wire body is provided with a support part for supporting an intermediate part of the operating wire.

This configuration permits easy operation of the operating wire.

Besides, in the intravascular foreign matter removing wire according to the present invention, preferably, the maximum outer diameter of the second catching section is smaller than the maximum outer diameter of the first catching section.

This configuration has the merit that damages to the inside surface of the blood vessel can be prevented from being generated.

In addition, in the intravascular foreign matter removing wire according to the present invention, preferably, the first catching section and the second catching section are connected to each other by a connecting wire.

This configuration makes it possible to more assuredly catch and remove the foreign matter present inside a blood vessel.

Besides, in the intravascular foreign matter removing wire according to the present invention, preferably, at least one of the first catching section and the second catching section has antislipping means for preventing the foreign matter caught from slipping.

This configuration ensures that in the case where the first catching section has the antislipping means, friction between the first catching section 3 and a foreign matter caught by the first catching section 3 can be increased, so that the foreign matter can be more assuredly held (caught). Besides, in the case where the second catching section has the antislipping means, also, substantially the same effect as in the case of the first catching section having the antislipping means can be obtained.

In addition, in the intravascular foreign matter removing wire according to the present invention, preferably, at least one of the first catching section and the second catching section has a plurality of flexible cilia.

This configuration ensures that in the case where the first catching section has the cilia, the foreign matter is entangled with the cilia and, therefore, the foreign matter can be securely prevented from coming off from the first catching section, so that the foreign matter can be caught more assuredly. In addition, in the case where the second catching section has the cilia, also, substantially the same effect as in the case of the first catching section having the cilia can be obtained.

Besides, in the intravascular foreign matter removing wire according to the present invention, preferably, at least one of the first catching section and the second catching section is composed of an alloy which shows super-elasticity in vivo.

This configuration ensures that in the case where the first catching section is composed of such an alloy, for example, the first catching section can have sufficient flexibility and restoring property with regard to bending, so that deformation of the first catching section can be repeated while obviating the generation of a bending tendency by the excellent restoring property. In addition, in the case where the second catching section is composed of such an alloy, also, substantially the same effect as in the case of the first catching section can be obtained.

In addition, in the intravascular foreign matter removing wire according to the present invention, preferably, the wire body has a part varying in rigidity along the longitudinal direction of the wire body.

This configuration makes it possible to secure a higher safety while retaining the torque transmission performance, pushability and kink resistance (resistance to sharp bending) of the wire body.

In order to attain the above object, according to the present invention, there is provided a medical implement including an intravascular foreign matter removing wire as set forth in any of claims 1 to 15, and a catheter having a lumen capable of storing the intravascular foreign matter removing wire therein.

This makes it possible to assuredly catch and remove a foreign matter present inside a blood vessel.

BEST MODE FOR CARRYING OUT THE INVENTION

Now, the intravascular foreign matter removing wire and the medical implement according to the present invention will be described in detail below, based on some preferred embodiments shown in the accompanying drawings.

First Embodiment

Figure 1:
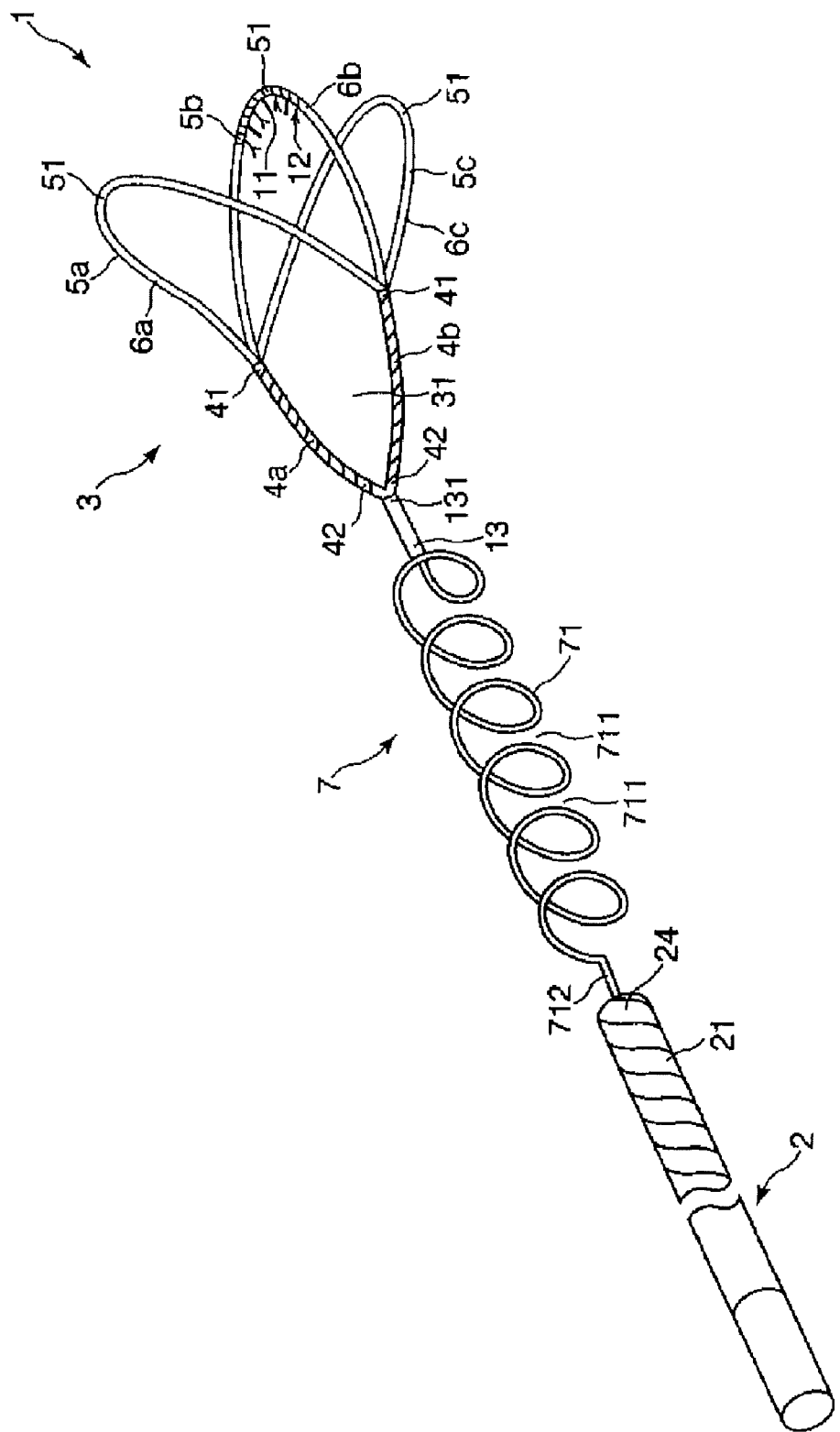
FIG. 1 is a perspective view of a first embodiment of the intravascular foreign matter removing wire according to the present invention.
Figure 2:
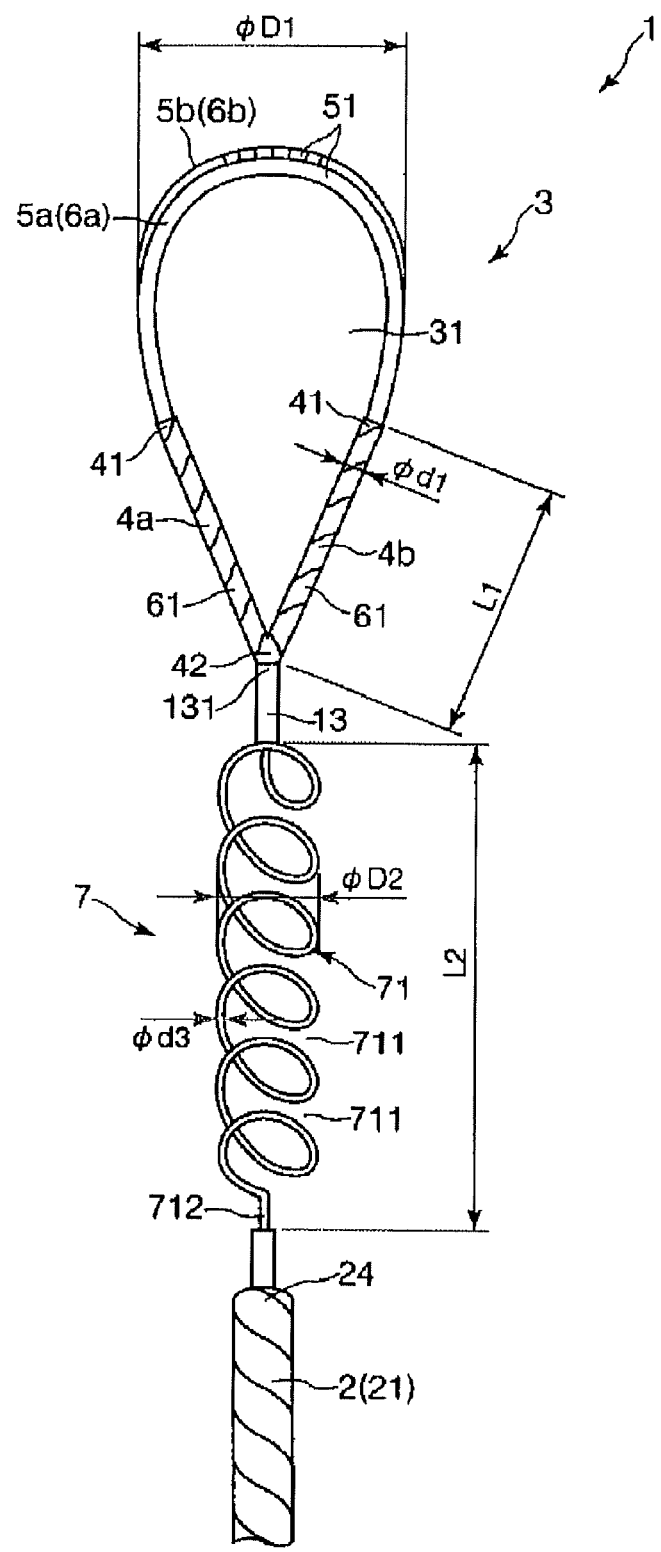
FIG. 2 is a plan view of the intravascular foreign matter removing wire shown in FIG. 1.
Figure 3:
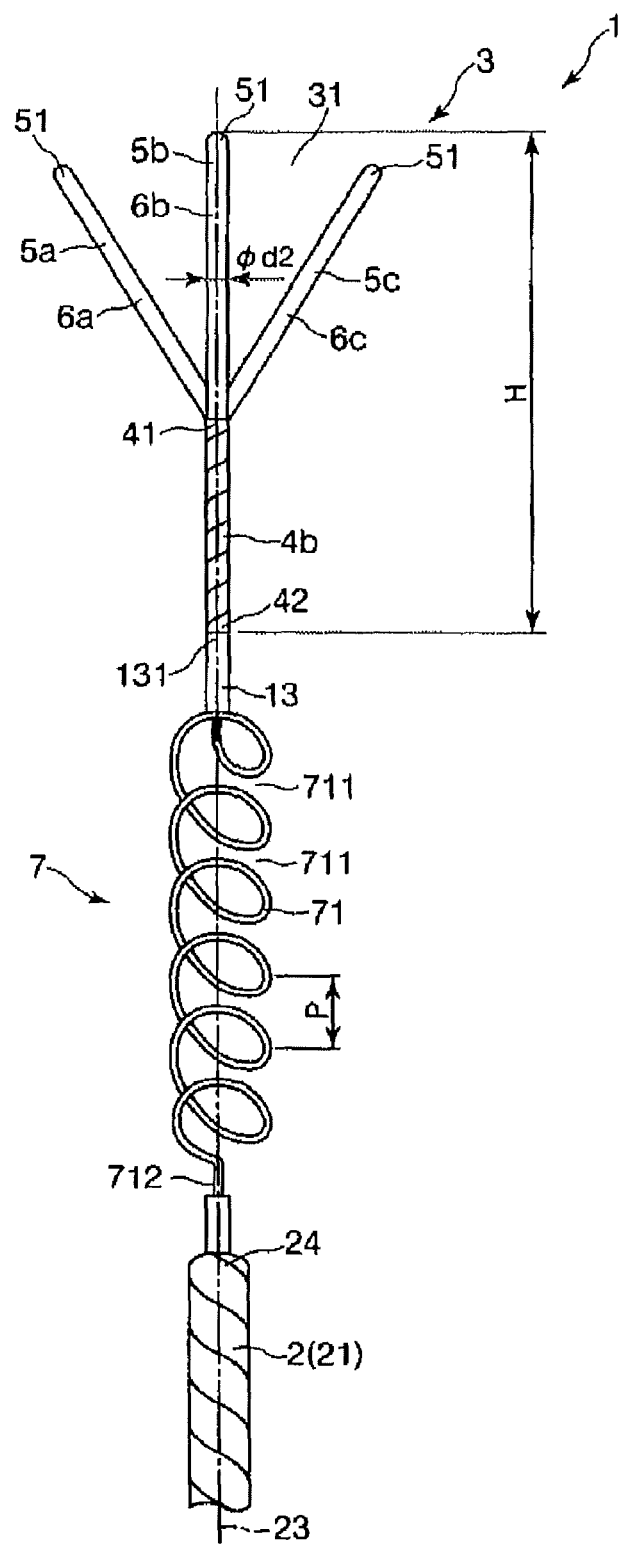
FIG. 3 is a side view of the intravascular foreign matter removing wire shown in FIG. 1.

FIG. 1 is a perspective view of a first embodiment of the intravascular foreign matter removing wire according to the present invention, FIG. 2 is a plan view of the intravascular foreign matter removing wire shown in FIG. 1, FIG. 3 is a side view of the intravascular foreign matter removing wire shown in FIG. 1, and FIGS. 4 to 7 are figures for illustrating a method of using the intravascular foreign matter removing wire shown in FIG. 1, in the sequence of steps.

Now, in the following description, the right side in FIG. 1 will be referred to as "the tip", the left side as "the base end", the upper side in FIGS. 2 and 3 will be referred to as "the tip", the lower side as "the base end", and the left side in FIGS. 4 to 7 will be referred to as "the tip", and the right side as "the base end".

The intravascular foreign matter removing wire 1 shown in FIG. 1 is catching and removing a foreign matter which would cause thrombosis, such as a thrombus, a blood clot, etc. (hereinafter referred to as "the embolus 200") present inside a blood vessel 100.

In this embodiment, description will be made by taking, as an example of the embolus 200, an embolus consists of a central (core-forming) core part 210, and an adherent part 220 adhering to the outside surface of the core part 210. The core part 210 is comparatively hard, while the adherent part 220 is comparatively soft.

The intravascular foreign matter removing wire 1 has a flexible long wire body 2, a first catching section 3 located on the tip side of the wire body 2, a second catching section 7 located in the vicinity of and on the base end side of the first catching section 3, and a connecting wire 13 connecting the first catching section 3 and the second catching section 7 to each other.

Now, the configurations of the components will be described.

The wire body 2 shown in FIG. 1 has appropriate rigidity and elasticity (flexibility) over the whole length thereof.

The structure of the wire body 2 is not particularly limited, and may be, for example, a body consists of a single wire, a body obtained by binding a plurality of wires, a hollow body, a body of a multilayer structure, a body having a core member and a coil wound around the core member, a combination of these, or the like.

The material constituting the wire body 2 is not particularly limited, and may be any one of various metallic materials, various plastics and the like, which may be used either singly or in combination.

In addition, the length of the wire body 2 has a preferable value which varies depending on the case such as the position, diametral size or the like of the blood vessel 100 of concern, and, in general, the length is preferably about 500 to 4000 mm, more preferably about 1500 to 2200 mm.

Besides, the outer diameter (diametral size) of the wire body 2 has a preferable value which varies depending on the case such as the position, diametral size or the like of the blood vessel 100 of concern, and, in general, the average outer diameter is preferably 0.1 to 2.0 mm, more preferably 0.25 to 0.9 mm.

Further, the wire body 2 preferably has a first portion located on the base end side and comparatively hard, a third portion located on the tip side and comparatively flexible, and a second portion located between the first portion and the third portion and varying in flexibility. In other words, the wire body 2 is preferably a wire body of which the rigidity (flexural rigidity, torsional rigidity or the like) is gradually reduced (varied) from the base end toward the tip thereof, i.e., along the londitudinal direction of the wire body 2. This configuration ensures that an operation on the hand side is securely transmitted to the tip part 24, feedability inside the blood vessel 100 and operability at a bent portion of the blood vessel 100 are excellent, and it is possible to enhance the flexibility of the tip part 24 and to prevent damages to the blood vessel 100 from being generated. In other words, a higher safety can be secured while retaining the torque transmission performance, pushability and kink resistance (resistance to sharp bending) of the wire body 2.

The wire body 2 may be provided on its outside surface (surface) with a coating layer for lessening the frictional resistance between the outside surface thereof and the inside surface of a catheter 8 (described later). This ensures that insertion and evulsion of the wire body 2 into and from the catheter 8 can be conducted more smoothly. Examples of the coating layer include a coating layer composed of a fluororesin such as polytetrafluoroethylene or the like (Teflon coat ("Teflon" is a registered trademark)), a hydrophilic polymer coat showing lubricity when wetted, etc.

The first catching section 3 is a section for catching the core part 210 of the embolus 200. As shown in FIGS. 1 to 3, the first catching section 3 is composed of two branch wire parts 4a and 4b branched from the tip of the connecting wire 13, a plurality of (in this embodiment, three) filament parts 5a, 5b and 5c bridgingly disposed between the two branch wire parts 4a and 4b.

In this embodiment, the branch wire parts 4a, 4b and the filament parts 5a, 5b, 5c are composed of three loop wires 6a, 6b, 6c provided in loop form (ring form) starting from the tip of the connecting wire 13. The loop wires 6a, 6b, 6c are each provided so as to extend from the tip of the connecting wire 13 in the tip direction (distal direction), to be bent back toward the base end in a loop form, and to return to the tip of the connecting wire 13. Incidentally, the loop wires 6a, 6b, 6c are substantially the same in shape, and, therefore, the loop wire 6a will be described representatively.

As shown in FIG. 1, the branch wire part 4a is composed of a stranded wire part formed by integrally collecting and stranding the portions on the one base end side of the loop wires 6a, 6b, 6c.

In addition, similarly, the branch wire part 4b is composed of a stranded wire part formed by integrally collecting and stranding the portions on the other base end side of the loop wires 6a, 6b, 6c.

The filament parts 5a, 5b, 5c are so configured that the portions on the tip side of the loop wires 6a, 6b, 6c are spaced from each other. Specifically, as shown in FIG. 3, the loop wires 6a, 6c are bent (or curved) to the outer sides (the left and right sides in FIG. 3) at their intermediate portions, and the portions on the tip side of the bent parts form the filament parts 5a, 5c, respectively.

Now, the configurations of the branch wire parts 4a, 4b and the filament parts 5a, 5b, 5c will be described below.

As shown in FIG. 1, the branch wire parts 4a, 4b are each in a filamentous shape, and has a base end part 42 thereof fixed (firmly attached) to a tip part 131 of the connecting wire 13. The method of fixation is not particularly limited; for example, the fixation can be achieved by winding the base end parts 42 of the branch wire parts 4a, 4b around a tip part of the connecting wire 13, and brazing and soldering, welding, adhesion with an adhesive, or the like is applied to this portion.

The branch wire parts 4a, 4b as above are configured to be elastically displaceable (deformable), and have flexibility.

As shown in FIG. 1, three filament parts 5a, 5b, 5c in a filamentous shape are bridgingly provided between the tip part 41 of the branch wire part 4a and the tip part 41 of the branch wire part 4b. The filament parts 5a, 5b, 5c have their central portions in an arch shape (curved shape) so curved as to bulge to the tip side, and are connecting the tip part 41 of the branch wire part 4a and the tip part 41 of the branch wire part 4b to each other, with their arch-shaped top parts 51 spaced from each other (see FIGS. 2 and 3).

Since the filament parts 5a, 5b, 5c thus configured are provided, damages to the inside wall 100a of a blood vessel 100 can be prevented from being generated, and a higher safety can be obtained. In addition, at the time of catching the embolus 200 (the core part 210), the embolus 200 once caught can be prevented from slipping off (coming off) from the tip side.

As shown in FIG. 3, the filament part 5b is substantially located on a plane passing through the center axis 23 of the wire body 2 (the plane perpendicular to the surface of sheet of FIG. 3). Specifically, the filament part 5b is seen to be substantially overlapped with the center axis 23 of the wire body 2.

In addition, the filament parts 5a, 5b are so inclined that the distance from the center axis 23 of the wire body 2 thereto increases as one goes in the tip direction (distal direction). Specifically, in side view shown in FIG. 3, the filament part 5a is inclined toward the left tip side, while the filament 5c is inclined toward the right tip side.

Besides, the first catching section 3 is provided with a foreign matter catching space 31 for catching the embolus 200, in such a manner as to be surrounded by the branch wire parts 4a, 4b and the filament parts 5a, 5b, 5c constituting the first catching section 3.

Since the first catching section 3 configured as above is provided, the core part 210 of the embolus 200 can be easily stored into the first catching section 3 (the foreign matter catching space 31), so that the core part 210 can be caught assuredly.

The second catching section 7 is a portion for catching the adherent part 220 of the embolus 200. As shown in FIGS. 1 to 3, the second catching section 7 is comprised of a filamentous body 71 extending on the tip side of a tip part 24 of the wire body 2. The filamentous body 71 is coil-like (spiral) in shape, and a gap 711 is provided between those portions of the filamentous body 71 which are adjacent to each other in the longitudinal direction of the intravascular foreign matter removing wire 1.

Figure 7:
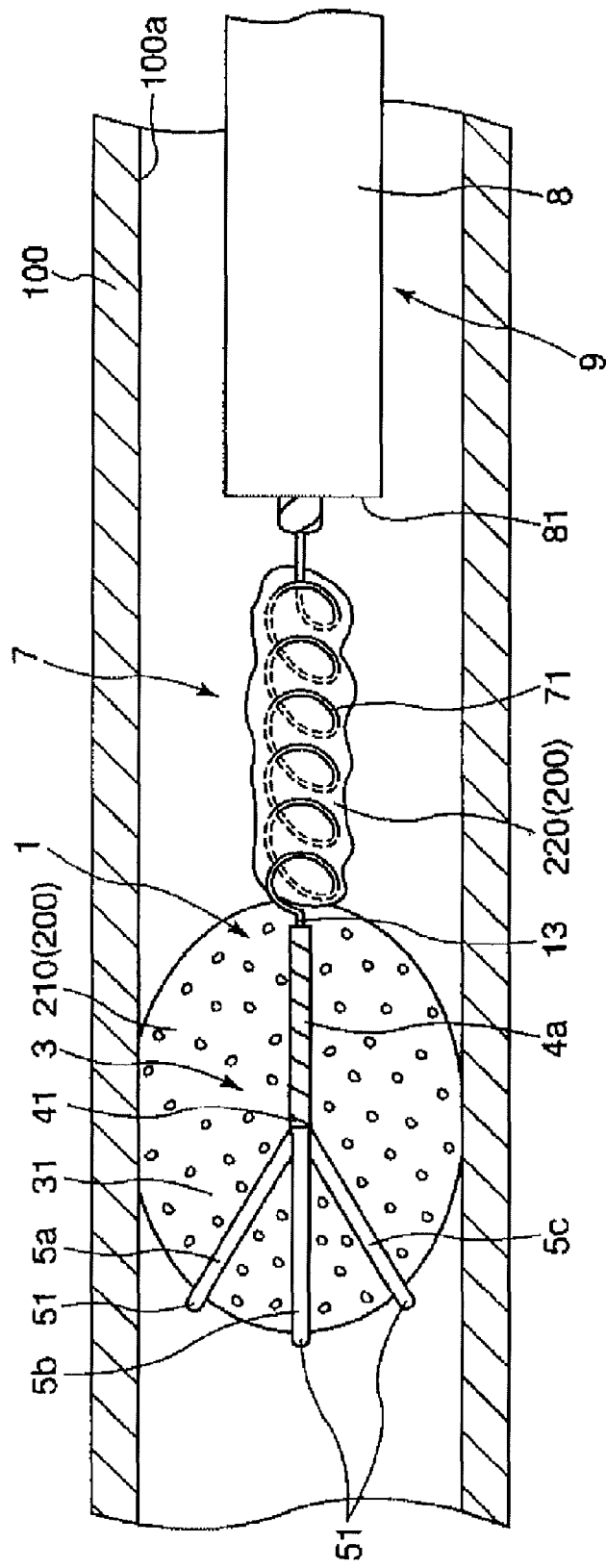
FIG. 7 is a figure for illustrating the method of using the intravascular foreign matter removing wire shown in FIG. 1, in the sequence of steps.

The provision of the second catching section 7 configured as above ensures that when the embolus 200 is caught, the adherent part 220 of the embolus 200 comes into the gap 711, so that the adherent part 220 can be arrested (caught) (see FIG. 7).

In addition, as shown in FIG. 2, the maximum outer diameter $\phi D2$ of the second catching section 7 is preferably smaller than the maximum outer diameter $\phi D1$ of the first catching section 3. This ensures that a plurality of catching parts (for example, the spiral parts of the second catching section 7) can be arrayed without spoiling the passing performance inside the catheter 8. Besides, damages to the blood vessel wall (inside wall 100a) can be prevented from being generated.

In addition, the second catching section 7 is preferably more flexible than the first catching section 3. This ensures that the second catching section 7 can more assuredly catch the comparatively soft adherent part 220 of the embolus 200, and the first catching part 3 can more assuredly catch the comparatively hard core part 210 of the embolus 200.

Besides, the structure of the second catching section 7 (the filamentous body 7) is not particularly limited; for example, the structure may be a structure composed of a single wire, a structure obtained by bundling a plurality of single wires, a hollow structure, a multilayer structure, a combination of these, or the like.

Further, the second catching section 7 is disposed with its base end part 712 fixed (firmly attached) to the tip part 24 of the wire body 2. The method of fixation is not particularly limited; for example, the fixation can be achieved by winding a base end part 712 of the second catching section 7 around the tip part 24 of the wire body 2, and brazing and soldering, welding, adhesion with an adhesive, or the like is applied to this portion.

In this embodiment, the tip part 24 of the wire body 2 is provided with a coil 21 for covering the part, fixed (brazed and soldered) to the wire body 2, of the second catching section 7. The outside surface of the coil 21 is smooth, which provides a higher safety. The coil 21 is preferably formed, for example, by winding a platinum wire or the like.

In addition, the filamentous body 71 constituting the second catching section 7 and the connecting wire 13 is preferably formed by deforming a single wire. This makes it possible to reduce the number of component parts constituting the intravascular foreign matter removing wire 1. Besides, the intravascular foreign matter removing wire 1 has flexibility, so that the intravascular foreign matter removing wire 1 can satisfactorily reach a thin (diametrically small) portion of the inside of the blood vessel 100.

In the first catching section 3, the average length L1 of the branch wire parts 4a, 4b is not particularly limited; for example, in the case of catching a embolus 200 (thrombus) present in a cerebral blood vessel, in general, the average length L1 is preferably about 1.0 to 10.0 mm, more preferably about 2.5 to 9.0 mm.

In addition, the average outer diameter $\phi d1$ is not particularly limited; for example, in the case of catching an embolus 200 (thrombus) present in a cerebral blood vessel, in general, the average outer diameter $\phi d1$ is preferably about 0.04 to 0.5 mm, more preferably 0.06 to 0.2 mm.

In the filament part 5b, the average distance H between the base ends of the branch wire parts 4a, 4b and the top part 51 is not particularly limited; for example, in the case of catching an embolus 200 (thrombus) present in a cerebral blood vessel, in general, the average distance H is preferably not less than 7 mm, more preferably 7 to 10 mm.

Besides, the average outer diameter $\phi d2$ of the filament parts 5a, 5b, 5c is not particularly limited; for example, in the case of catching an embolus 200 (thrombus) present in a cerebral blood vessel, in general, the average outer diameter φd2 is preferably 0.05 to 0.5 mm, more preferably about 0.1 to 0.4 mm.

In addition, in the second catching section 7, the average inter-loop distance P between adjacent loop portions of the filamentous body 71 is not particularly limited; for example, in the case of catching an embolus 200 (thrombus) present in a cerebral blood vessel, the average inter-loop distance P is preferably about 1 to 20 mm, more preferably about 1 to 8 mm.

Besides, in the second catching section 7, the maximum outer diameter φD2 is not particularly limited; for example, in the case of catching an embolus 200 (thrombus) present in a cerebral blood vessel, the maximum outer diameter φD2 is preferably about 1 to 5 mm, more preferably about 1 to 3 mm.

In addition, in the second catching section 7, the length L2 of the second catching section 7 has a preferable value which varies depending on the case such as the position, diametral size or the like of the blood vessel 100 of concern; for example, in the case of catching an embolus 200 (thrombus) present in a cerebral blood vessel, the length L2 is preferably about 1 to 30 mm, more preferably about 5 to 15 mm.

Besides, the number of loops (the number of turns) in the second catching section 7 is not particularly limited; for example, in the case of catching an embolus 200 (thrombus) present in a cerebral blood vessel, the number of loops is preferably about 3 to 16, more preferably about 6 to 10.

In addition, the materials constituting the first catching section 3 (the branch wire parts 4a, 4b and the filament parts 5a, 5b, 5c) and the second catching section 7 (the filamentous body 71) are preferably radiopaque materials. The radiopaque materials are not particularly limited, and examples thereof include gold, platinum, platinum-iridium alloys, tungsten, tantalum, palladium, lead, silver, and alloys, compounds and the like containing at least one of them.

With such radiopaque materials used, the state of the core part 210 (the embolus 200) caught by the first catching section 3 and the state of the adherent part 220 (the embolus 200) caught by the second catching section 7 can be easily checked under fluoroscopy or the like.

In addition, the materials constituting the first catching section 3 and the second catching section 7 are preferably alloys showing pseudo-elasticity (inclusive of alloys showing super-elasticity (hereinafter referred to as "super-elastic alloys")) in vivo (at least at the body temperature (around 37° C.)).

The alloys showing pseudo-elasticity (hereinafter referred to as "pseudo-elastic alloys") include any shape of tensile stress-strain curves, in which transformation points such as As, Af, Ms, Mf, etc. may be conspicuously measurable or non-measurable, and thus include all the alloys that are largely deformed (strained) under a stress and will return substantially to the initial shape thereof upon removal of the stress.

The pseudo-elastic alloys include the super-elastic alloys. Preferable compositions of the super-elastic alloys include Ni—Ti based alloys such as Ni—Ti alloys containing 49 to 59 atomic % of Ni; Cu—Zn alloys containing 38.5 to 41.5 wt % of Zn; Cu—Zn—X alloys (X is at least one of Be, Si, Sn, Al, and Ga) containing 1 to 10 wt % of X; and Ni—Al alloys containing 36 to 38 atomic % of Al. Among these alloys, particularly preferred are the Ni—Ti based alloys.

With such a pseudo-elastic alloy used, the first catching section 3 and the second catching section 7 can have sufficient flexibility and restoring property with regard to bending, and the first catching section 3 and the second catching section 7 can be deformed repeatedly while preventing generation of a bending tendency by the excellent restoring property.

In addition, the first catching section 3 and the second catching section 7 are preferably provided with antislipping means for preventing the embolus 200 caught from slipping off (coming off) from the first catching section 3 and the second catching section 7.

This makes it possible to increase the friction between the first catching section 3 and the core part 210 caught by the first catching section 3 and, therefore, to hold (catch) the core part 210 more assuredly. Besides, it is possible to increase the friction between the second catching section 7 and the adherent part 220 caught by the second catching section 7 and, therefore, to hold (catch) the core part 210 more assuredly.

The antislipping means is not particularly limited; for example, the antislipping means can be formed by coating with a rubber or other elastic material having a comparatively high frictional coefficient, or by forming minute recesses and projections (inclusive of a rough surface) by sandblasting or the like.

In addition, the outer surfaces (surfaces) of the first catching section 3 (the filament parts 5a, 5b, 5c) and the second catching section 7 (the filamentous body 71) may be provided with such a coating layer as mentioned in the description of the wire body 2 above. This ensures that insertion and evulsion into and from the catheter 8 can be performed smoothly.

As shown in FIG. 1, the filament part 5b is provided with a plurality of projections 11 projecting into the foreign matter catching space 31.

The method for forming each of the projections 11 is not particularly limited; for example, the projection 11 may be formed by winding one end side of a flexible filamentous body (wire) around the filament part 5b and minutely projecting one end part of the filamentous body.

Incidentally, the material constituting each of the projections 11 is not particularly limited; for example, various metallic material, various plastic and the like can be used either singly or in combination.

In addition, the length (average) of the projections 11 is not particularly limited; for example, the length is preferably 0.1 to 5 mm, more preferably 0.5 to 2 mm.

As shown in FIG. 1, the filament part 5b is provided with a plurality of flexible fine cilia 12 projecting in the foreign matter catching space 31. The fine cilia 12 are preferably softer than the projections 11.

The method for forming each of the fine cilia 12 is not particularly limited; for example, the fine cilia 12 can be formed by winding a cilium body having cilia 12 around the filament part 5b, by application of electronic flocking, or the like method.

Incidentally, the material constituting the fine cilia 12 is not particularly limited. Examples of the material which can be used include radiolucent fibers of Dacron (polyester), polyglycolic acid, polylactic acid, fluoropolymer (polytetrafluoroethylene), nylon (polyamide), cotton, silk, etc., and polymers (metallic yawns coated with radiolucent fibers, metallic yawns coated with radiopaque fibers), etc.

In addition, the length (average) of the fine cilia 12 is not particularly limited; for example, the length is preferably 0.1 to 5 mm, more preferably 0.5 to 3 mm.

When the projections 11 and the fine cilia 12 thus configured are formed (provided), the core part 210 is pierced by the projections 11 or entangled with the fine cilia 12, so that the core part 210 can be securely prevented from coming off from the foreign matter catching space 31, and the embolus 200 can be caught more assuredly.

Incidentally, the area where the projections 11 are provided is not limited to the filament part 5b; for example, the filament parts 5a and 5c may also be provided with the projections 11.

In addition, the area where the fine cilia 12 are provided is not limited to the filament part 5b; for example, the filament parts 5a and 5c may also be provided with the fine cilia 12.

Besides, in the case where the second catching section 7 is composed of a pseudo-elastic alloy, the second catching section 7 may, entirely or partly, be composed of a pseudo-elastic alloy.

In addition, while the branch wire parts 4a, 4b and the filament parts 5a, 5b, 5c are composed of continuous loop wires 6a, 6b, 6c in this embodiment, the branch wire parts and the filament parts in the present invention may be formed by connecting (joining) separate members. In that case, the method for fixing the filament parts to the branch wire parts may be any method, and examples of the method include brazing and soldering, welding, adhesion with an adhesive, etc.

Besides, the loop wires 6a, 6b, 6c constituting the branch wire parts 4a, 4b may not necessarily be stranded as in this embodiment, and may be in a simply collected state (simply bundled state).

Incidentally, the medical implement 9 according to the present invention has such an intravascular foreign matter removing wire 1 as above-described, and the catheter 8 provided with a lumen 82 capable for storing the intravascular foreign matter removing wire 1 therein.

Now, an example of the method of using the intravascular foreign matter removing wire 1 according to the present invention will be described in detail below.

Figure 4:
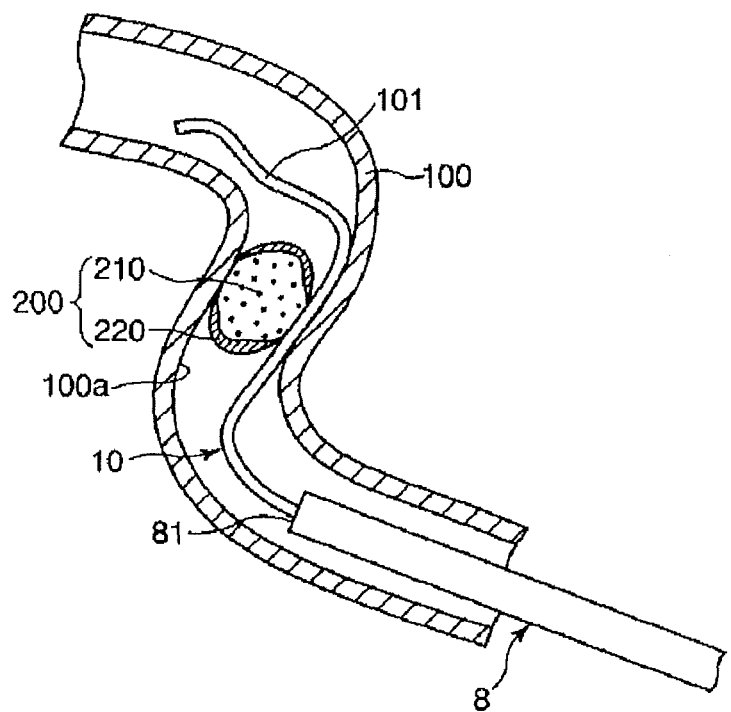
FIG. 4 is a figure for illustrating a method of using the intravascular foreign matter removing wire shown in FIG. 1, in the sequence of steps.

[1] FIG. 4 shows the condition where an embolus 200 such as a thrombus is plugging a blood vessel 100 to thereby block the bloodstream. The embolus 200 is pressed against the inside wall 100a of the blood vessel 100 by the blood pressure, and is in a hardly movable state. The embolus 200 is composed of a comparatively hard core part 210 and a comparatively soft adherent part 220.

The catheter (micro-catheter) 8 and a guide wire 10 inserted in the lumen 82 of the catheter 8 are inserted into the blood vessel 100, and a tip part 101 of the guide wire 10 protruded from a tip opening 81 of the catheter 8 is inserted into the depth (the distal side) relative to the embolus 200. Specifically, there is established a condition where the tip part 101 of the guide wire 10 is passed through the gap between the embolus 200 and the inside wall 100a of the blood vessel 100 beyond the embolus 200. This operation can be carried out more easily by use of, for example, a micro guide wire having excellent lubricity as the guide wire 10.

Figure 5:
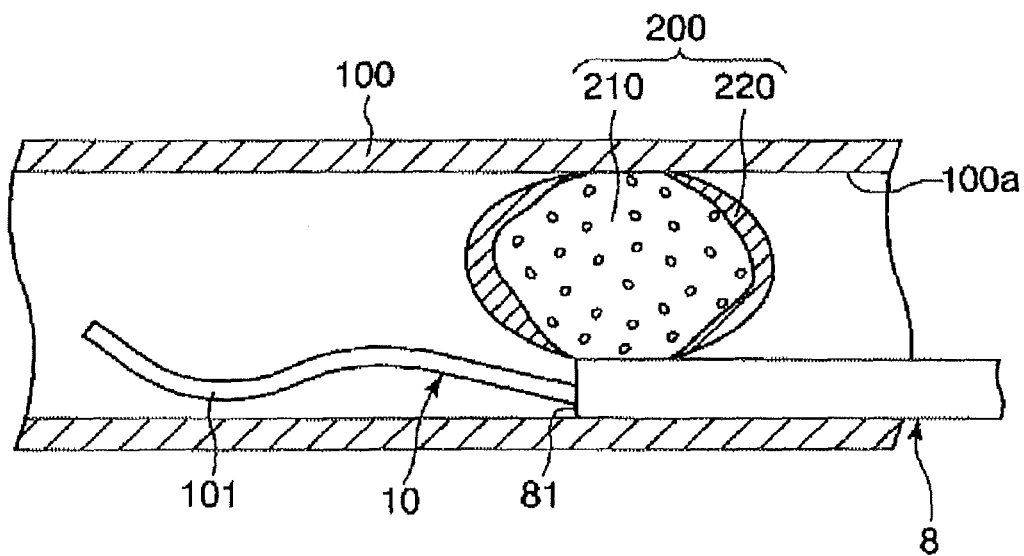
FIG. 5 is a figure for illustrating the method of using the intravascular foreign matter removing wire shown in FIG. 1, in the sequence of steps.

[2] When the tip part 101 of the guide wire 10 is passed beyond the embolus 200, the catheter 8 is moved forward relative to the guide wire 10, to bring a tip part of the catheter 8 into the gap between the embolus 200 and the inside wall 100a of the blood vessel 100, as shown in FIG. 5. In this instance, the tip part of the catheter 8 enters into the gap smoothly along the guide wire 10, and, therefore, this operation can be carried out easily.

Incidentally, in the conventional cure, a thrombolitic is made to flow retrogressively through the catheter 8 in this condition, so as to accelerate the thrombolysis. However, it has been recognized from doctors' frequent experiences that certain thrombi cannot be dissolved by thrombolytics and that a long time may be taken for the dissolution of the thrombus. The present invention is of use even in such a case.

Figure 6:
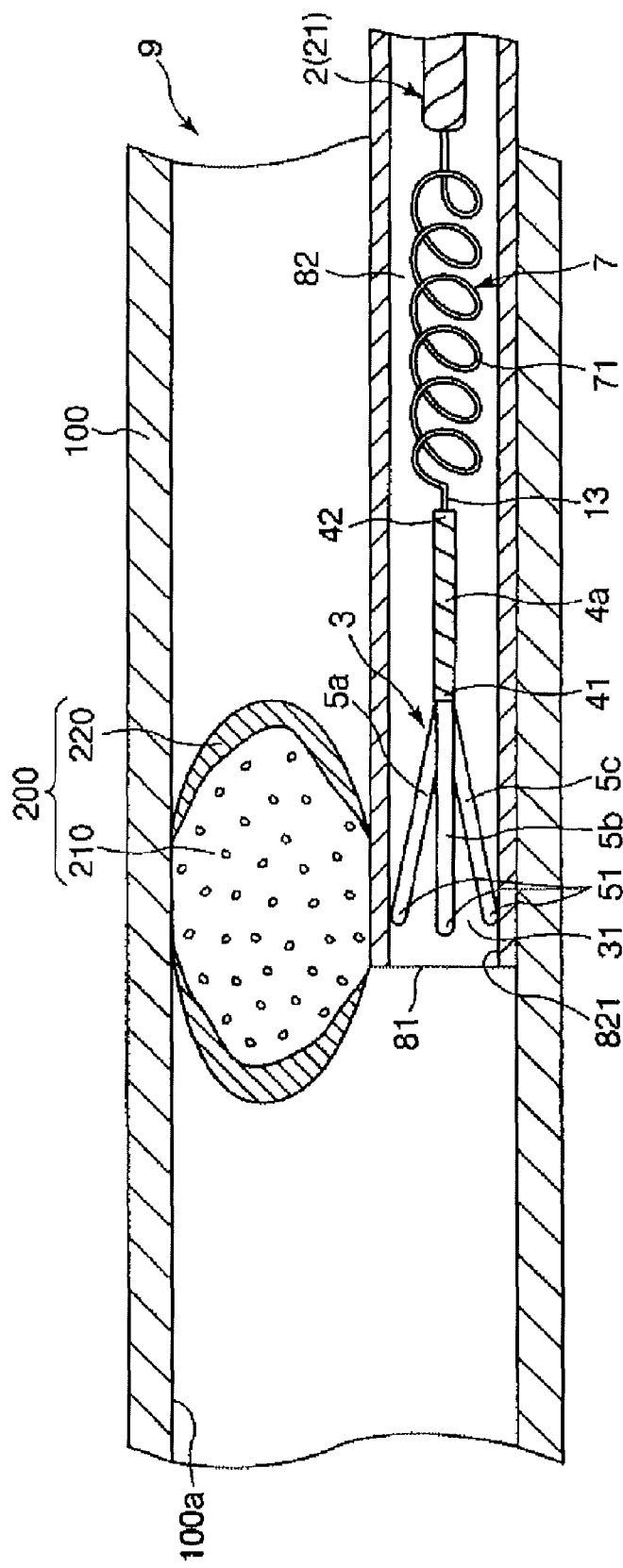
FIG. 6 is a figure for illustrating the method of using the intravascular foreign matter removing wire shown in FIG. 1, in the sequence of steps.

[4] Starting from the condition shown in FIG. 5, the guide wire 10 is evulsed, and the intravascular foreign matter removing wire 1 is inserted into the lumen 82 of the catheter 8. In this instance, as shown in FIG. 6, the first catching section 3 is restricted by the inside wall surface 821 defining the lumen 82, and is in a contracted state in which the tip part 41 of the branch wire part 4a and the tip art 41 of the branch wire part 4b are close to each other.

When the first catching section 3 and the second catching section 7 are protruded from the tip opening 81 of the catheter 8, the first catching part 3 having been in the contracted state inside the catheter 8 is automatically developed due to its own elasticity, into a natural state.

[5] Starting from the condition where the first catching section 3 and the second catching section 7 are protruded from the tip opening 81 of the catheter 8 as above-mentioned, the catheter 8 is slightly moved in the base end direction (the proximal direction) to withdraw the tip part of the catheter 8 to the proximal side of the embolus 200, and thereafter the intravascular foreign matter removing wire 1 is moved in the base end direction (the proximal direction), whereon the second catching section 7 is caught (entangled) in the adherent part 220 of the embolus 200.

With the intravascular foreign matter removing wire 1 moved further in the base end direction (the proximal direction), the core part 210 is caught (stored) in the manner of being scooped up into the foreign matter catching space 31 of the first catching section 3, as shown in FIG. 7. Specifically, the core part 210 enters into the foreign matter catching space 31 from the upper side in FIG. 7.

Thus, the embolus 200 is assuredly caught by the first catching section 3 and the second catching section 7.

[6] While maintaining the condition shown in FIG. 7, the intravascular foreign matter removing wire 1 is evulsed together with the catheter 8. As a result, the embolus 200 is recovered (removed) into a master guiding catheter or sheath introducer (not shown).

In addition, as above-mentioned, the first catching section 3 and the second catching section 7 are connected to each other through the connecting wire 13.

In the case where, for example, the connecting wire 13 is omitted and the first catching section 3 and the second catching section 7 are connected directly to each other, the first catching section 3 and the second catching section 7 are too close to each other. Therefore, the first catching section 3 reaches the position of the embolus 200 before the catching of the adherent part 220 of the embolus 200 by the second catching section 7 is finished, so that it is difficult to assuredly catch the core part 210 of the embolus 200.

However, with the connecting wire 13 provided, the first catching section 3 and the second catching section 7 are appropriately spaced from each other. Therefore, after the adherent part 220 of the embolus 200 is assuredly caught by the second catching section 7, the core part 210 of the embolus 200 can be caught assuredly by the first catching section 3.

In addition, the outer diameter $\phi D1$ of the first catching section 3 in the contracted state is not particularly limited; for example, the outer diameter $\phi D1$ is preferably not more than 0.012 inch, more preferably not more than 0.018 inch.

Second Embodiment

Figure 8:
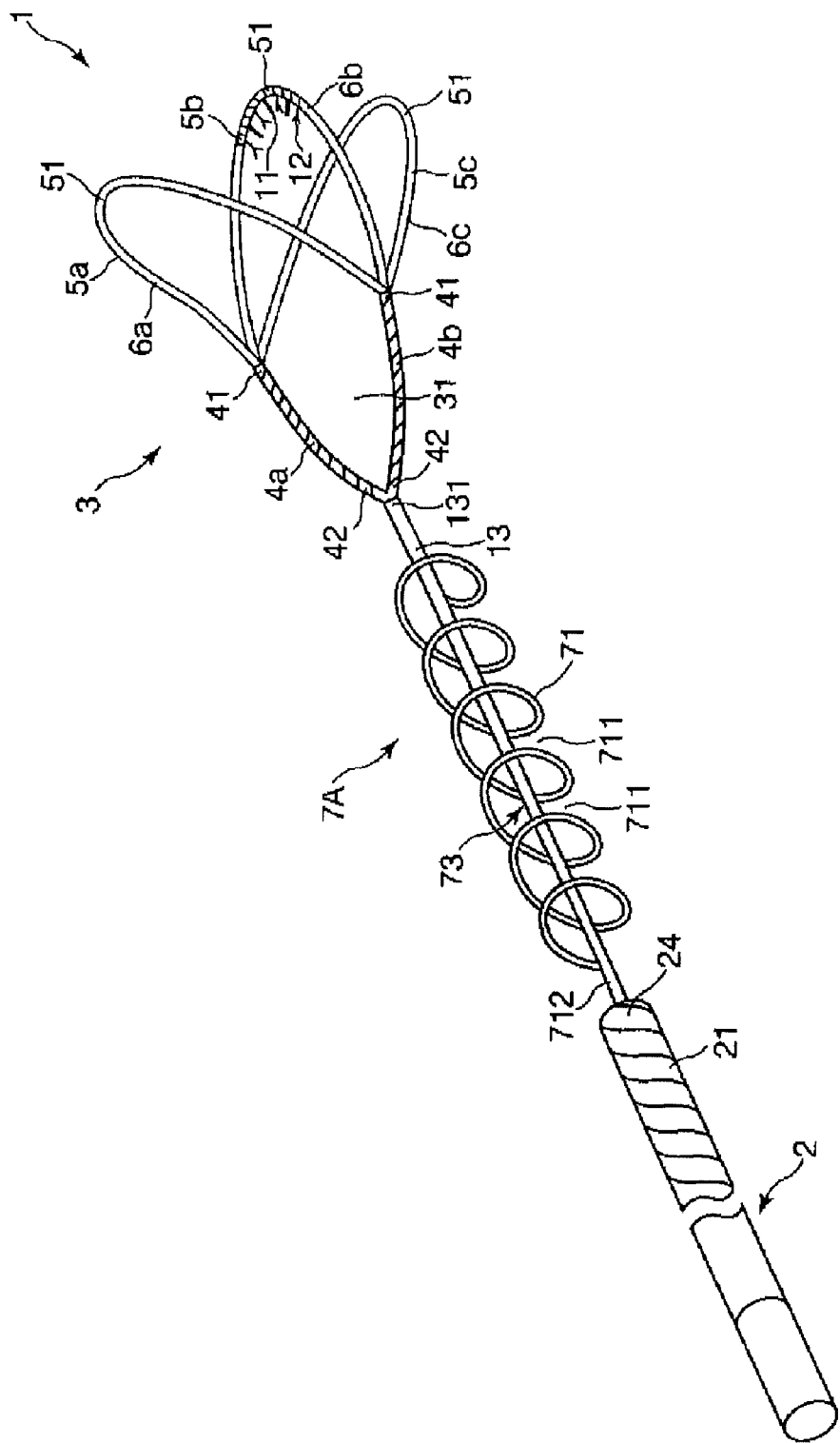
FIG. 8 is a perspective view of a second embodiment of the intravascular foreign matter removing wire according to the present invention.

FIG. 8 is a perspective view of a second embodiment of the intravascular foreign matter removing wire according to the present invention.

Now, the second embodiment of the intravascular foreign matter removing wire according to the present invention will be described below, referring to the figure. The following description will be centered on the differences from the first embodiment described above, and descriptions of the same items as those in the first embodiment will be omitted.

This embodiment is the same as the first embodiment above, except for the configuration of the second catching section.

As shown in FIG. 8, the second catching section 7A is composed of a coil-like filamentous body 71 and a substantially rectilinear filamentous body 73.

The filamentous body 73 is bridgingly provided between both end parts of the filamentous body 71 so as to pass through the inside of the filamentous body 71.

Meanwhile, the second catching section 7 (the filamentous body 71) in the first embodiment above is easily extended in the longitudinal direction of the intravascular foreign matter removing wire 1.

On the other hand, in the second catching section 7A in this embodiment, the filamentous body 73 prevents or restrain the filamentous body 71 from easily extending in the longitudinal direction of the intravascular foreign matter removing wire 1. The second catching section 7A with such a configuration is effective in the case where, for example, extension of the filamentous body 71 is not desired.

Incidentally, the filamentous body 73 is disposed, with both end parts thereof fixed (firmly attached) respectively to both end parts of the filamentous body 71. The method of fixation is not particularly limited; for example, the fixation can be performed by winding each end part of the filamentous body 73 around each end part of the filamentous body 71, and applying brazing and soldering, welding, adhesion with an adhesive, or the like to this portion.

Third Embodiment

Figure 9:
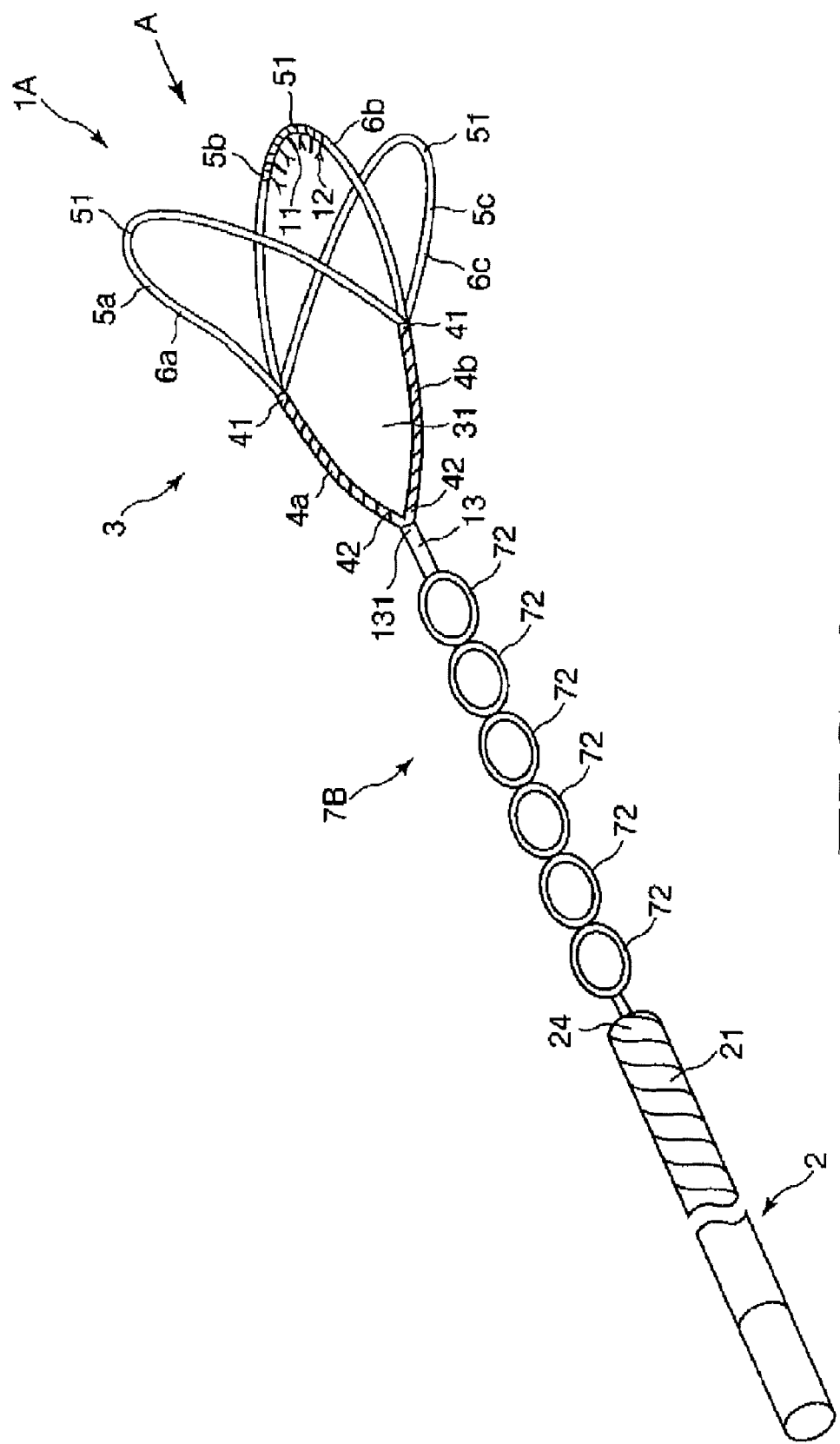
FIG. 9 is a perspective view of a third embodiment of the intravascular foreign matter removing wire according to the present invention.
Figure 10:
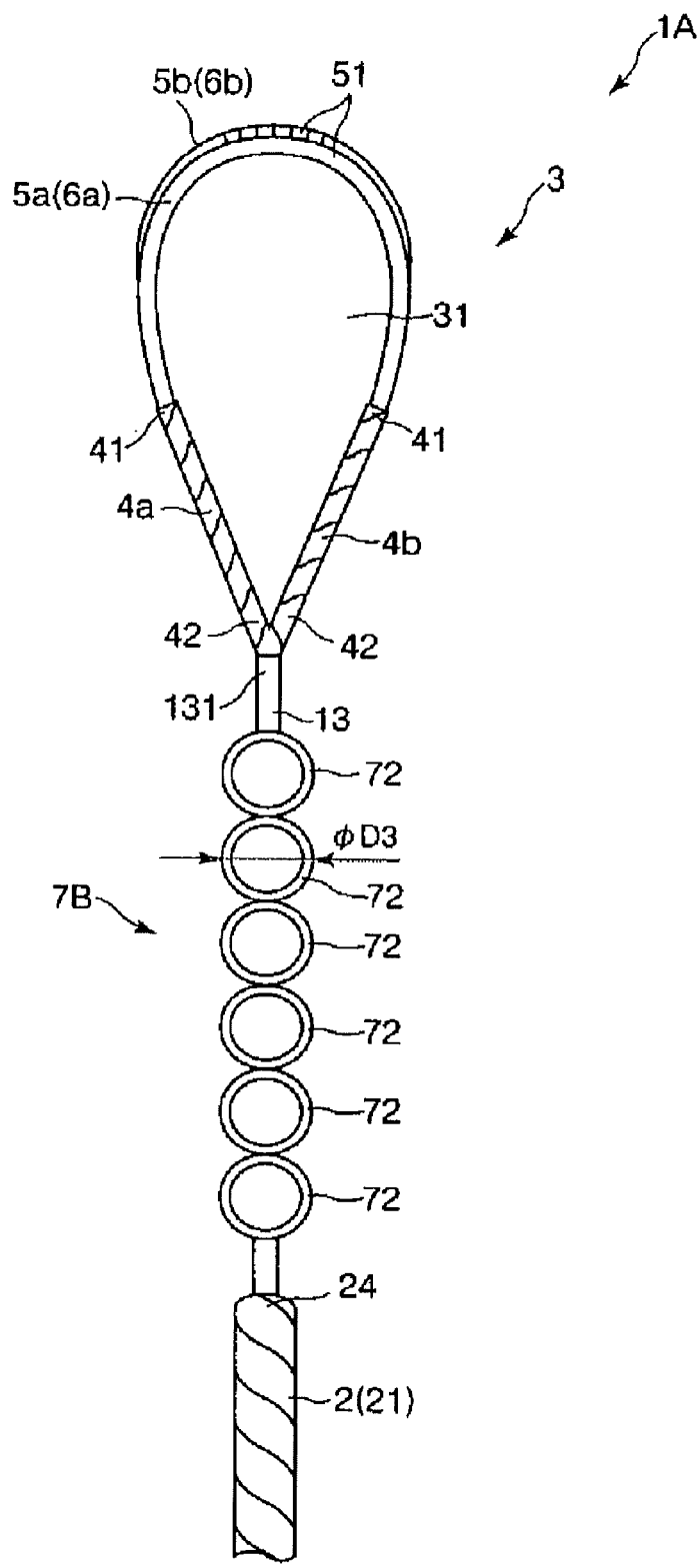
FIG. 10 is a plan view of the intravascular foreign matter removing wire shown in FIG. 9.
Figure 11:
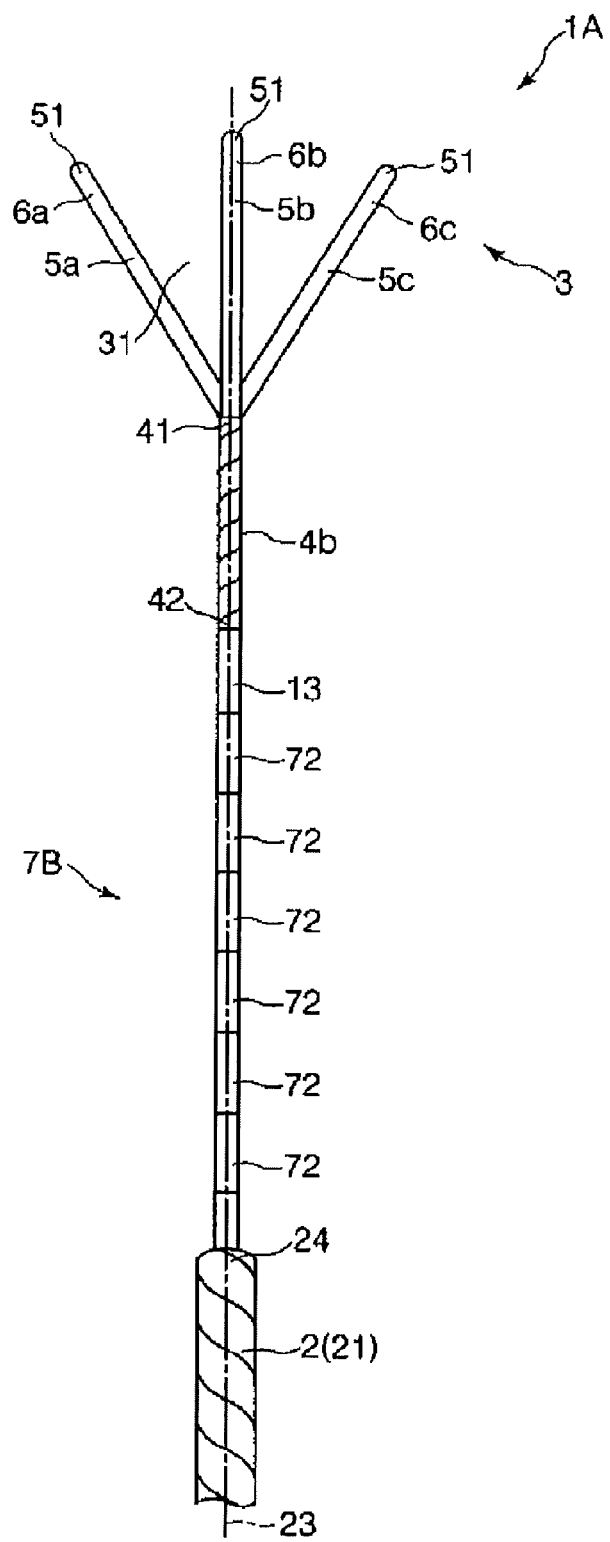
FIG. 11 is a side view of the intravascular foreign matter removing wire shown in FIG. 9.

FIG. 9 is a perspective view of a third embodiment of the intravascular foreign matter removing wire according to the present invention, FIG. 10 is a plan view of the intravascular foreign matter removing wire shown in FIG. 9, and FIG. 11 is a side view of the intravascular foreign matter removing wire shown in FIG. 9.

Now, the third embodiment of the intravascular foreign matter removing wire according to the present invention will be described below, referring to these figures. The following description will be centered on the differences from the first embodiment described above, and descriptions of the same items as those in the first embodiment will be omitted.

This embodiment is the same as the first embodiment above, except for the configuration of the second catching section.

As shown in FIG. 9, in the intravascular foreign matter removing wire 1A in this embodiment, the second catching section 7B is comprised of a plurality of (in this embodiment, six) loop wires 72 which are circular (loop-like) in shape. These loop wires 72 are arranged (arrayed) along the longitudinal direction of the wire body 2.

In addition, the outer diameters TD3 of the loop wires 72 are substantially equal.

Besides, the six loop wires 72 are so formed that their respective formation directions are substantially the same, when the second catching section 7B is viewed from the tip side in the longitudinal direction of the wire body 2 (viewed along arrow A in FIG. 9). In other words, the six loop wires 72 are so formed as to constitute a single filamentous body (to appear as a single filamentous body), in side view, as shown in FIG. 11.

The second catching section 7B thus configured ensures that the adherent part 220 of an embolus 200 enters into each of the loop wires 72 and, therefore, the adherent part 220 can be arrested more assuredly.

Incidentally, the outer diameter φD3 of the loop wires 72 is not particularly limited; for example, in the case of catching an embolus 200 (thrombus) present in a cerebral blood vessel, the outer diameter φD3 is preferably about 1.0 to 3.0 mm, more preferably about 1.0 to 2.0 mm.

In addition, the number of the loop wires 72 formed is not limited to six; for example, in the case of catching an embolus 200 (thrombus) present in a cerebral blood vessel, the number is preferably about 1 to 30, more preferably about 2 to 15.

Fourth Embodiment

Figure 12:
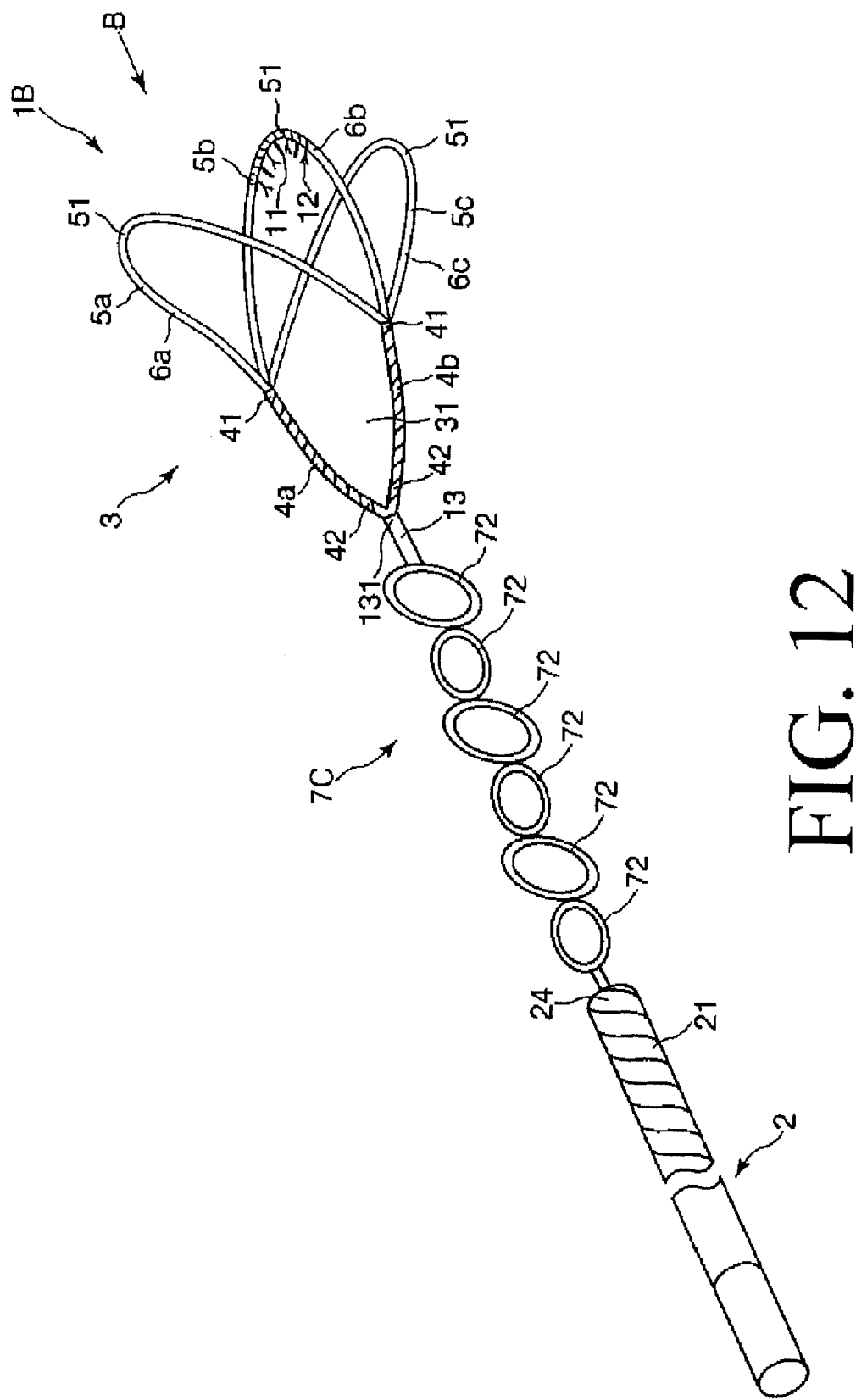
FIG. 12 is a perspective view of a fourth embodiment of the intravascular foreign matter removing wire according to the present invention.
Figure 13:
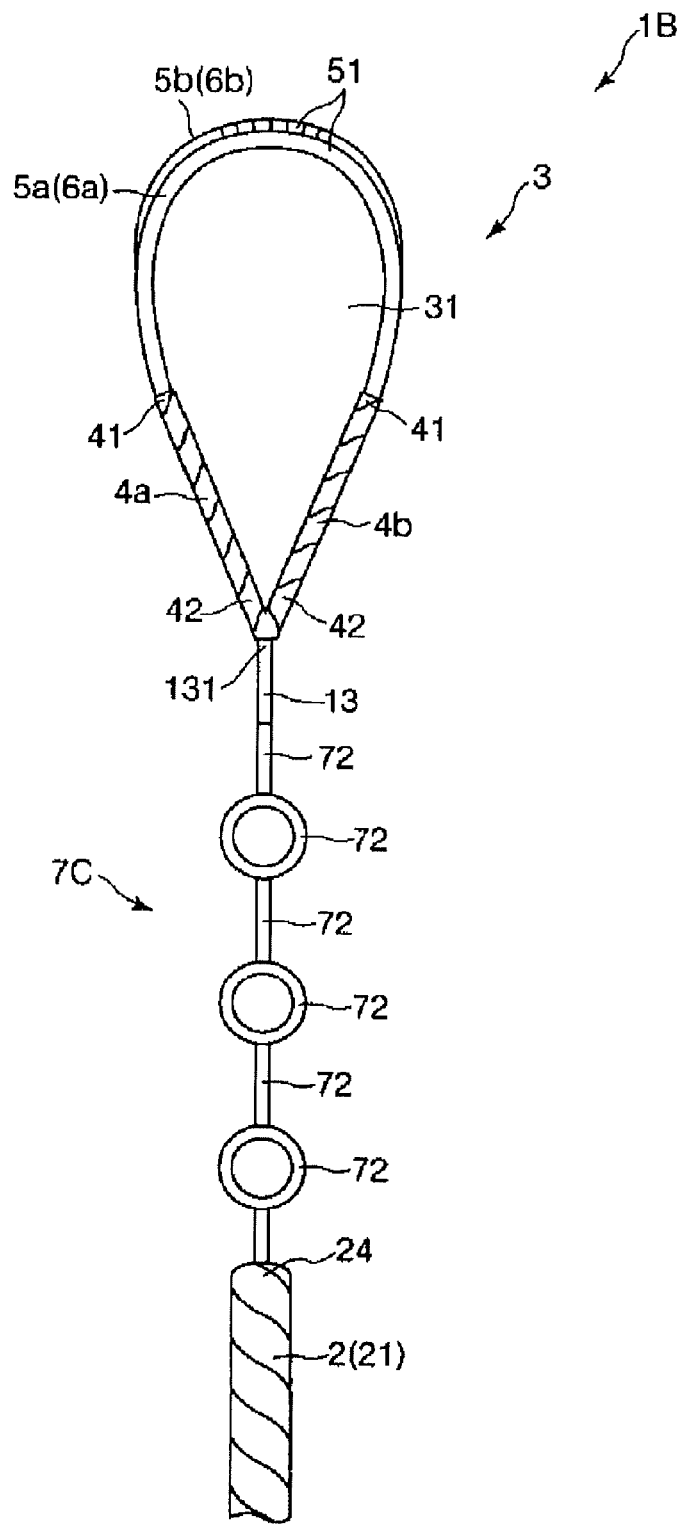
FIG. 13 is a plan view of the intravascular foreign matter removing wire shown in FIG. 12.
Figure 14:
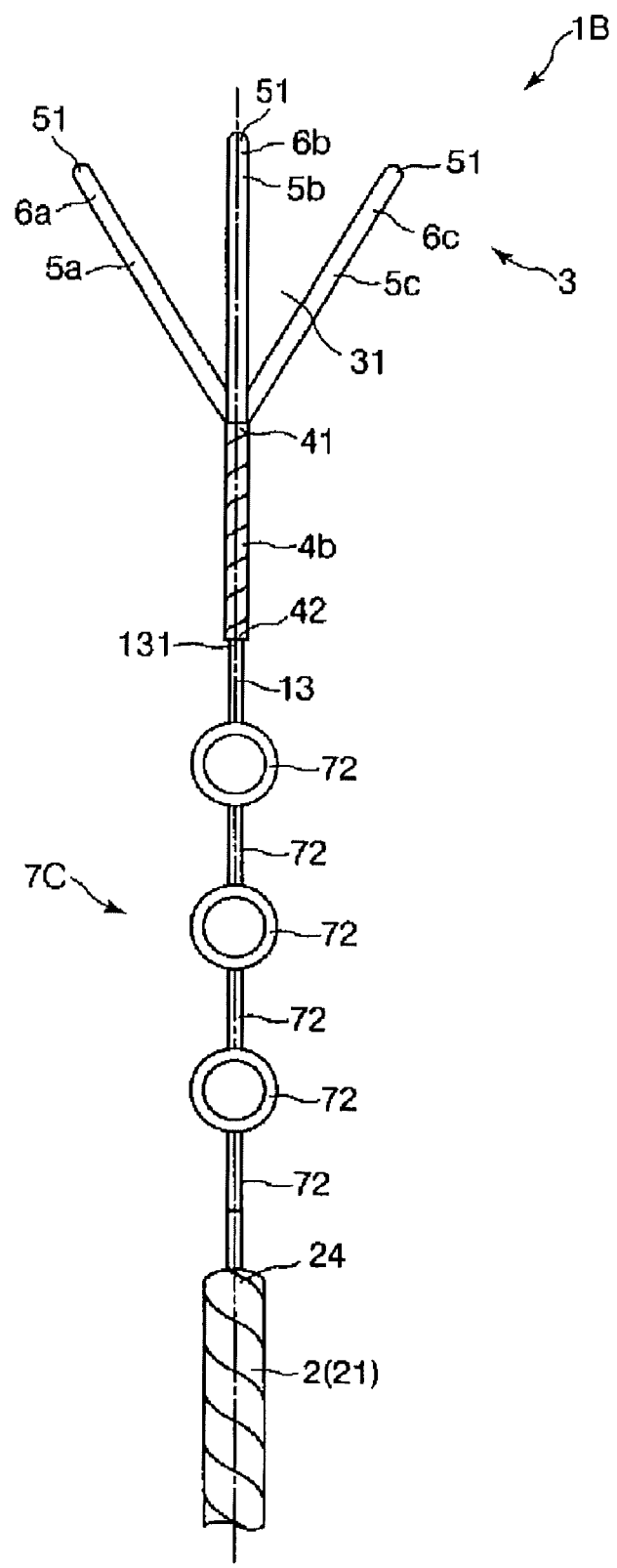
FIG. 14 is a side view of the intravascular foreign matter removing wire shown in FIG. 12.

FIG. 12 is a perspective view of a fourth embodiment of the intravascular foreign matter removing wire according to the present invention, FIG. 13 is a plan view of the intravascular foreign matter removing wire shown in FIG. 12, and FIG. 14 is a side view of the intravascular foreign matter removing wire shown in FIG. 12.

Now, the fourth embodiment of the intravascular foreign matter removing wire according to the present invention will be described below, referring to these figures. The following description will be centered on the differences from the third embodiment above, and descriptions of the same items as those in the third embodiment will be omitted.

This embodiment is the same as the third embodiment above, except for the shape of the second catching section.

As shown in FIG. 12, in the intravascular foreign matter removing wire 1B in this embodiment, when the second catching section 7C is viewed from the tip side in the longitudinal direction of the wire body 2 (viewed along arrow B in FIG. 12), the adjacent ones of the loop wires 72 are different from each other in formation direction; specifically, the adjacent ones of the loop wires 72 are at 90 degrees to each other. In other words, in the second catching section 7C, loop wires 72 having a formation direction parallel to the plane of sheet of FIG. 13 (FIG. 14) and loop wires 72 having a formation direction orthogonal to the plane of sheet of FIG. 13 (FIG. 14) are alternately arranged, in plan view and side view, as shown in FIGS. 13 and 14.

The second catching section 7C thus configured ensures that the adherent part 220 of an embolus 200 enters into each of the loop wires 72, so that the adherent part 220 can be arrested more assuredly.

Fifth Embodiment

Figure 15:
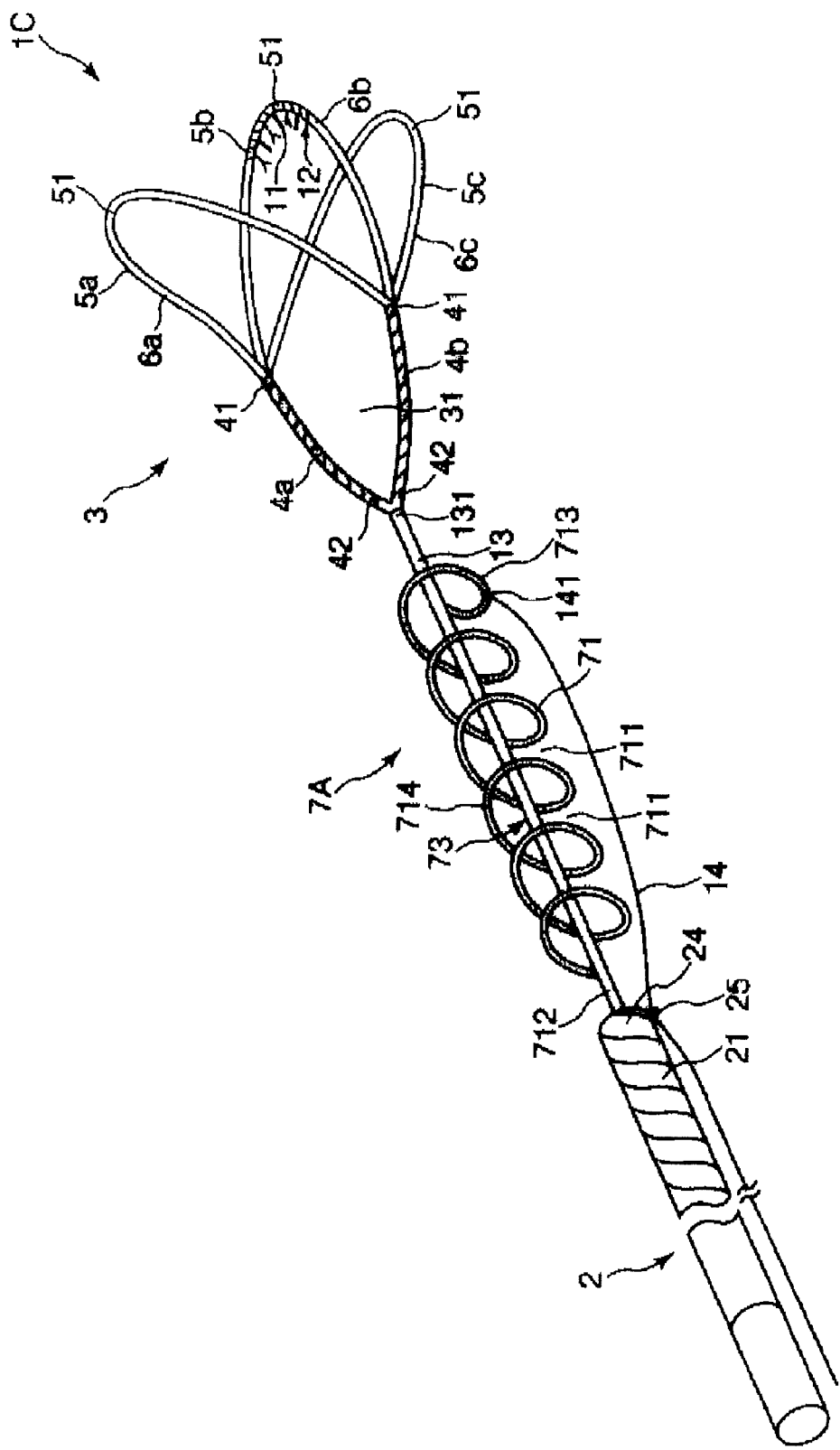
FIG. 15 is a perspective view of a fifth embodiment of the intravascular foreign matter removing wire according to the present invention.
Figure 16:
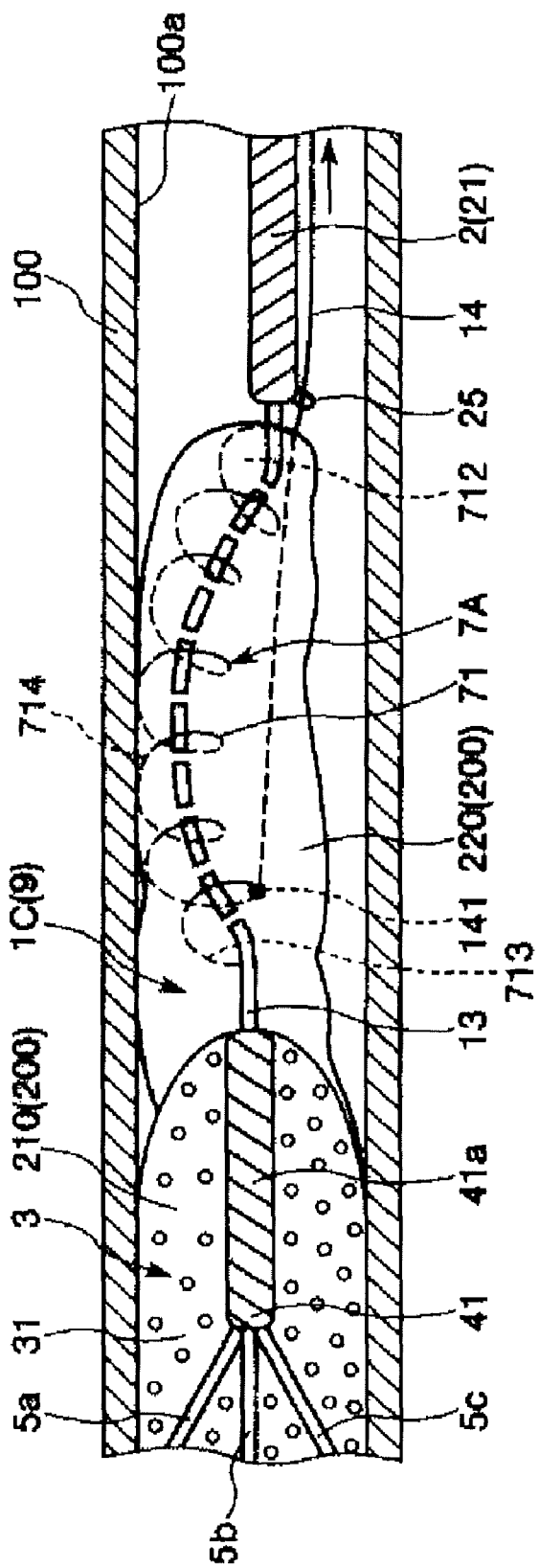
FIG. 16 is a figure showing an example of the condition in use of the intravascular foreign matter removing wire shown in FIG. 15.

FIG. 15 is a perspective view of a fifth embodiment of the intravascular foreign matter removing wire according to the present invention, and FIG. 16 is a figure showing an example of the condition in use of the intravascular foreign matter removing wire shown in FIG. 15.

Now, the fifth embodiment of the intravascular foreign matter removing wire according to the present invention will be described below, referring to these figures. The following description will be centered on the differences from the second embodiment described above, and descriptions of the same items as those in the second embodiment will be omitted.

This embodiment is the same as the second embodiment above, except that the intravascular foreign matter removing wire in this embodiment further has an operating wire.

The intravascular foreign matter removing wire 1C shown in FIG. 15 further has a flexible operating wire 14. As shown in FIG. 16, the operating wire 14 is so configured that the operating wire 14 can be pulled in the base end direction (the proximal direction) (in the direction of arrow in FIG. 16). This ensures that the second catching section 7A (the filamentous body 73) is deformed assuredly.

The operating wire 14 has its tip part 141 joined to a tip end part 713 of the second catching section 7A, and extends in the base end direction (the proximal direction) therefrom. Incidentally, the method of joining is not particularly limited; for example, the joining can be conducted by winding the tip part 141 of the operating wire 14 around a tip part 713 of the second catching part 7A, and applying brazing and soldering, welding, adhesion with an adhesive, or the like to this portion.

When the operating wire 14 thus configured is operated, the tip part 713 of the second catching section 7A is drawn toward the base end part 712, and the second catching section 7A is curved and deformed (deflected) to be arch-shaped as a whole. This ensures that, in the condition in use of the intravascular foreign matter removing wire 1C, a central part 714 of the second catching section 7A can be brought close to the inside wall 100a of a blood vessel 100. Therefore, in the case where an adherent part 202 (an embolus 200) is present in the vicinity of the inside wall 100a, the adherent part 202 can be caught assuredly.

In addition, the wire body 2 is provided with a support part (wire guide) 25 for supporting an intermediate part of the operating wire 14. The support part 25 is ring-like in shape, and the operating wire 14 is passed therethrough.

With such a support part 25 provided, when the operating wire 14 is pulled, the operating wire 14 is guided, so that the operation can be performed easily.

Besides, while the number of the second catching part 7A joined to the operating wire 14 is one in this embodiment, the number is not limited to one. For example, a plurality of such second catching sections 7A may be arranged side by side. In that case, when the operating wire 14 is pulled, the second catching sections 7A are curved and deformed in different directions (in radial directions of a blood vessel 100). This ensures that in the case where an adherent part 202 (an embolus 200) is present along the circumferential direction of the inside wall 100a of the blood vessel 100, the adherent part 202 can be collectively caught.

In addition, the material constituting the operating wire 14 is not particularly limited; for example, various metallic materials, various plastics and the like can be used either singly or in combination, like in the case of the wire body 2.

While the intravascular foreign matter removing wire and the medical implement according to the present invention have been described referring to their embodiments shown in the drawings, the present invention is not limited to the embodiments, and components of the intravascular foreign matter removing wire and the medical implement can be replaced by those which have arbitrary configurations and can exhibit the functions equivalent to the functions of the above-described components. Besides, arbitrary structures may be added.

In addition, the intravascular foreign matter removing wire and the medical implement according to the present invention may be those obtained by combining arbitrary two or more configurations (characteristic features) of the above-described embodiments.

For example, the second catching section in the third embodiment may be provided with the rectilinear filamentous body of the second embodiment.

In addition, the second catching section in the fourth embodiment may be provided with the rectilinear filamentous body of the second embodiment.

Besides, the number of the branch wire parts formed (arranged) is not limited to two, and may be three or more.

In addition, the number of the filament parts formed is not limited to three, and may be two or be four or more.

Besides, while the third embodiment and the fourth embodiment have been described by showing as an example the case where the outer diameters of the loop wires in the second catching section are equal, the present invention is not limited to this configuration, and the outer diameters of the loop wires may be different.

In addition, while the third embodiment and the fourth embodiment have been described by showing as an example the case where the loop shapes of the loop wires in the second catching section are nearly circular, the present invention is not limited to this configuration, and the loop shapes may be any of various shapes such as ellipse, flat oval, polygons, etc. and shapes obtained by combining these shapes, etc.

Besides, while the fourth embodiment has been described by showing as an example the case where the adjacent ones of the loop wires in the second catching section are at 90 degrees to each other, as viewed from the front side, the present invention is not limited to this configuration. The angle between the adjacent ones of the loop wires may be, for example, 30 degrees, 45 degrees or the like.

In addition, the intravascular foreign matter removing wires described in the first, third and fourth embodiments may each be provided with an operating wire substantially the same as that in the fifth embodiment. For example, the intravascular foreign matter removing wire in the first embodiment may be provided with an operating wire. In that case, when the operating wire is operated, the gap between the adjacent ones of the filamentous bodies in the second catching section (filamentous bodies) is reduced, i.e., the second catching section is deformed so as to be contracted. This ensures that the adherent part of an embolus can be caught in the state of being clamped between the adjacent ones of the filamentous bodies.

Besides, the first catching section and the second catching section are not limited to those each composed of an alloy which shows super-elasticity in vivo; for example, one of the first and second catching sections is composed of an alloy showing super-elasticity in vivo.

In addition, the configuration in which the first catching section and the second catching section are provided with antislipping means is not limitative; for example, one of the first and second catching sections may be provided with anti-slipping means.

Besides, the configuration in which only the first catching section is provided with the projections is not limitative; for example, the second catching section may also be provided with the projections, or only the second catching section may be provided with the projections.

In addition, the configuration in which only the first catching section is provided with the fine cilia is not limitative; for example, the second catching section may also be provided with the cilia, or only the second catching section may be provided with the cilia.

INDUSTRIAL APPLICABILITY the intravascular foreign matter removing wire according to the present invention includes the flexible long wire body, the first catching section located on the tip side of the wire body and operative to catch a foreign matter present inside a blood vessel, and the second catching section located in the vicinity of and on the base end side of the first catching section and operative to catch a foreign matter present inside a blood vessel. Therefore, the first catching section and/or the second catching section can assuredly catch a foreign matter in a blood vessel, and the foreign matter thus caught can be securely removed from the inside of the blood vessel. Particularly, in the case of a foreign matter which has a core-forming comparatively hard part and a comparatively soft part adhering to the surface of the hard part, the first catching section can catch the comparatively hard part, while the second catching section can catch the comparatively soft part, so that the intravascular foreign matter removing wire is effective. Therefore, the centesis implement according to the present invention has an industrial applicability.

The invention claimed is:

1. An intravascular foreign matter removing wire comprising:
    a flexible long wire body;
    a first catching section located on a tip side of the wire body and operative to catch a foreign matter present inside a blood vessel;
    a second catching section located in a vicinity of and on a base end side of said first catching section and operative to catch a foreign matter inside a blood vessel, the second catching section possessing a tip end part and a base end part, the tip end part of the second catching section being located closer to the first catching section than the base end part of the second catching section; and
    an operating wire possessing a tip end part directly connected to the tip end part of the second catching section, the operating wire being movable with respect to the first catching section so that movement of the operating wire in a base end direction away from the first catching section moves the tip end part of the second catching section.

2. The intravascular foreign matter removing wire as set forth in claim 1, wherein the tip end part of the second catching section is connected to a base end part of the first catching section by a connecting wire, the connecting wire possessing a base end part fixed to the tip end part of the second catching wire and a tip end part fixed to a base end part of the first catching section, said first catching section is composed of at least two spaced apart branch wire parts extending distally from the tip end part of the connecting wire, the at least two branch wire parts including a first branch wire part and a second branch wire part, the first and second branch wire parts each possessing a tip end part remote from the second catching section, the first catching section also being composed of a plurality of filament parts each having one end fixed to the tip end part of the first branch wire part and an opposite end fixed to the tip end part of the second branch wire part so that each of the filament parts extends between the first and second branch wire parts.

3. The intravascular foreign matter removing wire as set forth in claim 1, wherein said second catching section is coil-like in shape.

4. The intravascular foreign matter removing wire as set forth in claim 1, wherein said second catching section is composed of a plurality of loop-formed loop wires arrayed along the longitudinal direction of said wire body.

5. The intravascular foreign matter removing wire as set forth in claim 4, wherein said plurality of loop wires are so formed that their respective formation directions are substantially the same, when said second catching section is viewed from the tip side of the second catching section in said longitudinal direction of said wire body.

6. The intravascular foreign matter removing wire as set forth in claim 4, wherein at least adjacent ones of said loop wires are so formed that their respective formation directions are different, when said second catching section is viewed from the tip side in said longitudinal direction of said wire body.

7. The intravascular foreign matter removing wire as set forth in claim 1, wherein said second catching section is deformable.

8. The intravascular foreign matter removing wire as set forth in claim 7, wherein said wire body includes a ring-shaped portion, and wherein an intermediate part of the operating wire positioned external of the wire body passes through the ring-shaped portion to support the intermediate part of said operating wire.

9. The intravascular foreign matter removing wire as set forth in claim 1, wherein a maximum outer diameter of said second catching section is smaller than the maximum outer diameter of said first catching section.

10. The intravascular foreign matter removing wire as set forth in claim 1, wherein the base end part of said first catching section and the tip end part of said second catching section are connected to each other by a connecting wire.

11. The intravascular foreign matter removing wire as set forth in claim 10, wherein at least one of said first catching section and said second catching section has antislipping means for preventing said foreign matter caught from slipping.

12. The intravascular foreign matter removing wire as set forth in claim 1, wherein at least one of said first catching section and said second catching section has a plurality of flexible cilia.

13. The intravascular foreign matter removing wire as set forth in claim 1, wherein at least one of said first catching section and said second catching section is composed of an alloy which shows super-elasticity in vivo.

14. The intravascular foreign matter removing wire as set forth in claim 1, wherein said wire body has a part varying in rigidity along the longitudinal direction of said wire body.

15. A medical implement comprising:
    an intravascular foreign matter removing wire as set forth in claim 1; and
    a catheter having a lumen capable of storing said intravascular foreign matter removing wire therein.

16. An intravascular device for removing foreign matter from a bodily lumen, the intravascular device comprising:
    a flexible wire body having a distal end positionable inside the bodily lumen and a proximal end positionable outside the bodily lumen;
    a first catching section connected to the distal end of the wire body and configured to catch foreign matter inside the bodily lumen;
    a second catching section configured to catch foreign matter inside the bodily lumen, the second catching section comprising a first filamentous body and a second filamentous body, the second filamentous body surrounding the first filamentous body, the second filamentous body possessing a tip end part and a base end part, the tip end part of the second filamentous body being fixed to the first filamentous body and the base end part of the second filamentous body being fixed to the first filamentous body, the tip end part of the second filamentous body being located closer to the first catching section than the base end part of the second filamentous body; and
    an operating wire possessing a tip end part connected to the tip end part of the second filamentous body and movable in a base end direction to cause the second catching section to curve into an arc-shape.

17. The intravascular device of claim 16, wherein the second filamentous body comprises a coil-shaped filamentous body and the first filamentous body is a rectilinear filamentous body.

* * * * *